(12) United States Patent
Yoon et al.

(10) Patent No.: US 6,640,051 B1
(45) Date of Patent: Oct. 28, 2003

(54) THERMAL TREATMENT APPARATUS RADIATING LOW AND HIGH TEMPERATURE

(76) Inventors: Jung-Sun Yoon, #310-303 Shinbanpo 8cha Hanshin Apartment, Chamwon-Dong, Seocho-Gu, Seoul (KR), 137-797; Hee-Sun Yoon, #A-101 Miju Apartment, 302-54 Dongbuichon-Dong, Yongsan-Gu, Seoul (KR), 140-031

(*) Notice: Subject to any disclaimer, the term of this patent is extended or adjusted under 35 U.S.C. 154(b) by 59 days.

(21) Appl. No.: 10/031,348

(22) PCT Filed: Jul. 11, 2000

(86) PCT No.: PCT/KR00/00746
§ 371 (c)(1),
(2), (4) Date: Jan. 11, 2002

(87) PCT Pub. No.: WO01/03618
PCT Pub. Date: Jan. 18, 2001

(30) Foreign Application Priority Data

Jul. 13, 1999 (KR) .............................................. 99-28166
Jun. 15, 2000 (KR) ........................................ 2000-32858

(51) Int. Cl.[7] .................................................. F26B 3/30
(52) U.S. Cl. ........................ 392/412; 607/96; 250/494
(58) Field of Search ................................. 392/412, 418, 392/419, 422; 34/266; 250/435, 494; 606/9; 607/96, 101; 600/1; 378/207

(56) References Cited

U.S. PATENT DOCUMENTS

| | | | | |
|---|---|---|---|---|
| 4,309,616 A | * | 1/1982 | Wolf ............................ 250/494 |
| 5,046,495 A | | 9/1991 | Takahashi et al. | |
| 5,168,514 A | * | 12/1992 | Horton, Jr. et al. .......... 378/209 |
| 5,231,770 A | * | 8/1993 | Fertig .......................... 34/266 |
| 5,233,990 A | * | 8/1993 | Barnea ..................... 128/653.1 |
| 5,335,308 A | * | 8/1994 | Sorensen .................... 392/412 |
| 5,547,454 A | * | 8/1996 | Horn et al. ..................... 600/1 |
| 5,659,657 A | * | 8/1997 | Overdorf .................... 392/422 |
| 5,898,817 A | * | 4/1999 | Salmon et al. ............. 392/418 |
| 6,080,146 A | * | 6/2000 | Altshuler ........................ 606/9 |
| 6,122,550 A | * | 9/2000 | Kozhemiakian et al. .... 607/101 |
| 6,150,663 A | * | 11/2000 | Rosenthal ................... 250/435 |
| 6,226,454 B1 | * | 5/2001 | Couture ...................... 392/419 |
| 6,409,744 B1 | * | 6/2002 | Marchesi ..................... 607/96 |

FOREIGN PATENT DOCUMENTS

| | | |
|---|---|---|
| JP | 01-2658553 | 10/1989 |
| JP | 2-057274 | 2/1990 |
| JP | 03-094749 | 4/1991 |
| JP | 09-028821 | 2/1997 |
| KR | 1992-008972 | 6/1992 |
| KR | 1996-006803 | 3/1996 |
| KR | 1997-020129 | 5/1997 |

* cited by examiner

*Primary Examiner*—Teresa Walberg
*Assistant Examiner*—L Fastovsky
(74) *Attorney, Agent, or Firm*—Oppedahl & Larson, LLP (57) ABSTRACT

Disclosed is a thermal treatment apparatus radiating low and high temperature, which includes a low-temperature radiating section and a high-temperature radiating section, and can rotatably scan affected parts. Both the low and the high temperature radiating sections are rotatable. The thermal treatment apparatus according to the present invention further includes a controller, with which a user can adjust the period of time for radiating low and high temperature as well as for rotation of the low-temperature radiating section and the high-temperature radiating section. The low-temperature radiating section is connected to a cryo-pump, while the high-temperature radiating section comprises an infrared ray lamp or a far infrared ray lamp. The present invention is applicable to medical treatment, physical therapy, sterilization of cosmetics or pharmaceuticals, or to tests of critical temperature for survival of cells.

20 Claims, 5 Drawing Sheets

THERMAL TREATMENT APPARATUS RADIATING LOW AND HIGH TEMPERATURE

TECHNICAL FIELD

The present invention relates to a thermal treatment apparatus radiating low and high temperature. More particularly this invention relates to a thermal treatment apparatus radiating low and high temperature, which can repeatedly turn the period of time for radiating low temperature and high temperature by integrating a high-temperature radiating section with a low-temperature radiating section, and can rotatable treat the affected parts.

BACKGROUND ART

The conventional physical treatment apparatuses mostly radiate high temperature using infrared ray, etc., although there also exist some apparatuses radiating low temperature serving for particular purposes. Those apparatuses normally comprise a heat radiating section for radiating high or low temperature to affected parts, a stand for supporting the heat radiating section, and a control section for controlling the temperature or a period of time for thermal irradiation.

However, the conventional apparatuses radiating either high or low temperature only pose the problem of requiring two separate apparatuses for radiating both low and high temperature.

DISCLOSURE OF INVENTION

To solve the above problem, the present invention provides a thermal treatment apparatus radiating low and high temperature, in which radiation of low and high temperature can be repeatedly shifted in turns by manipulating a single control section integrating a high-temperature radiating section with a low-temperature radiating section, and irradiating the low and high temperature on the affected parts can be rotatably performed in horizontal and vertical directions.

The thermal treatment apparatus radiating low and high temperature mainly comprises a high-temperature radiating section, a low-temperature radiating section, and a control section. The high-temperature radiating section and the low-temperature radiating section are movable and can radiate low and high temperature. The user can control the period of time for radiating low and high temperature by the low-temperature radiating section and the high-temperature radiating section as well as for rotation thereof by the control section through manipulation.

The high-temperature radiating section can be embodied with an infrared ray lamp, while the low-temperature radiating section can be embodied with a cryo-pump. The period of time and cycles of radiating low and high temperature by the respective sections can be controlled by the control section. Therefore, the irradiating can be performed with appropriate period of time and cycles suitable for the affected parts. Moreover, the high-temperature radiating section and the low-temperature radiating section are rotatable in vertical and horizontal directions, thereby serving for a user convenience.

The thermal treatment apparatus according to the present invention comprises a high-temperature radiating section for radiating high temperature, a low-temperature radiating section for radiating low temperature, a shifting section for shifting to and from the high-temperature radiating section and the low-temperature radiating section, a high-temperature radiating time control section for controlling the on-time of the high-temperature radiating section, a low-temperature radiating time control section for controlling on-time of the low-temperature radiating section, and a shift control section for controlling the shifting time of the shifting section.

The high-temperature radiating section is either an infrared ray lamp or a far-infrared ray lamp, while the low-temperature radiating section radiates low temperature by being connected to the cryo-pump.

The shifting section is characterized in that a yoke supporting the high-temperature radiating section and the low-temperature radiating section is rotated according to a rotation of a motor. The shifting section is also characterized in that the high-temperature radiating section and the low-temperature radiating section perform a lineal movement in vertical or horizontal direction according to the rotation of the motor.

The shifting section is further characterized by performing a vertical movement according to a power cylinder, and a horizontal rotation according to a rotation of the horizontal rotating means.

The shifting section is also characterized by a main axle, on which the high-temperature radiating section and the low-temperature radiating section are mounted, and means for performing lineal reciprocating movements in horizontal direction centering around the main axle so as to irradiate low and high temperature onto the affected parts through lineal movements.

A shutter is installed at the low-temperature radiating section so as to be shut down when the radiation time of the low temperature is over, thereby completely blocking radiation of the low temperature remained in the low-temperature radiating section.

BRIEF DESCRIPTION OF THE DRAWINGS

The above objects and other advantageous features of the present invention will become more apparent with the following explanation made with reference to the accompanying drawings, in which.

BEST MODE FOR CARRYING OUT THE INVENTION

The following is a detailed description of the present invention made with reference to the best modes thereof.

(1) Best Mode 1

Figure 1:
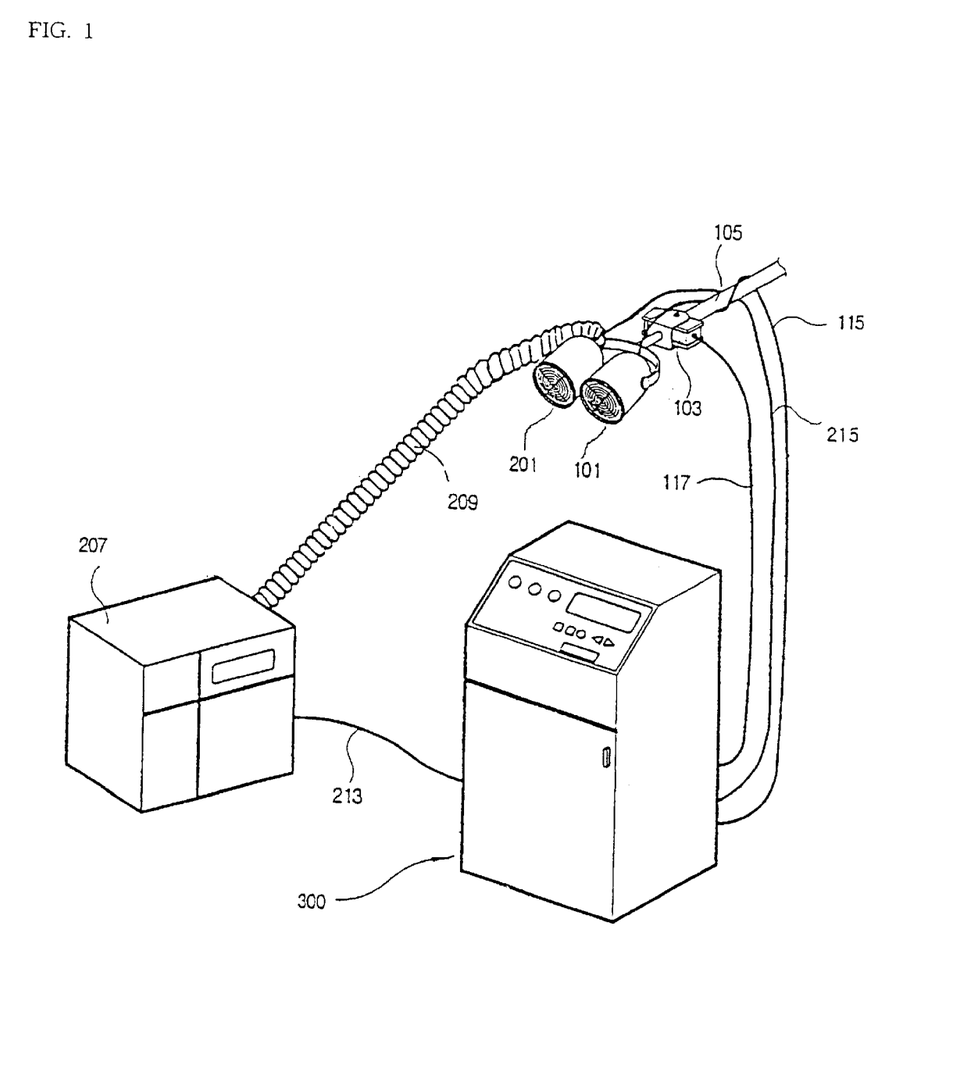
FIG. 1 is a view illustrating a comprehensive constitution of a thermal treatment apparatus radiating low and high temperature according to a best mode 1 of the present invention.
Figure 2:
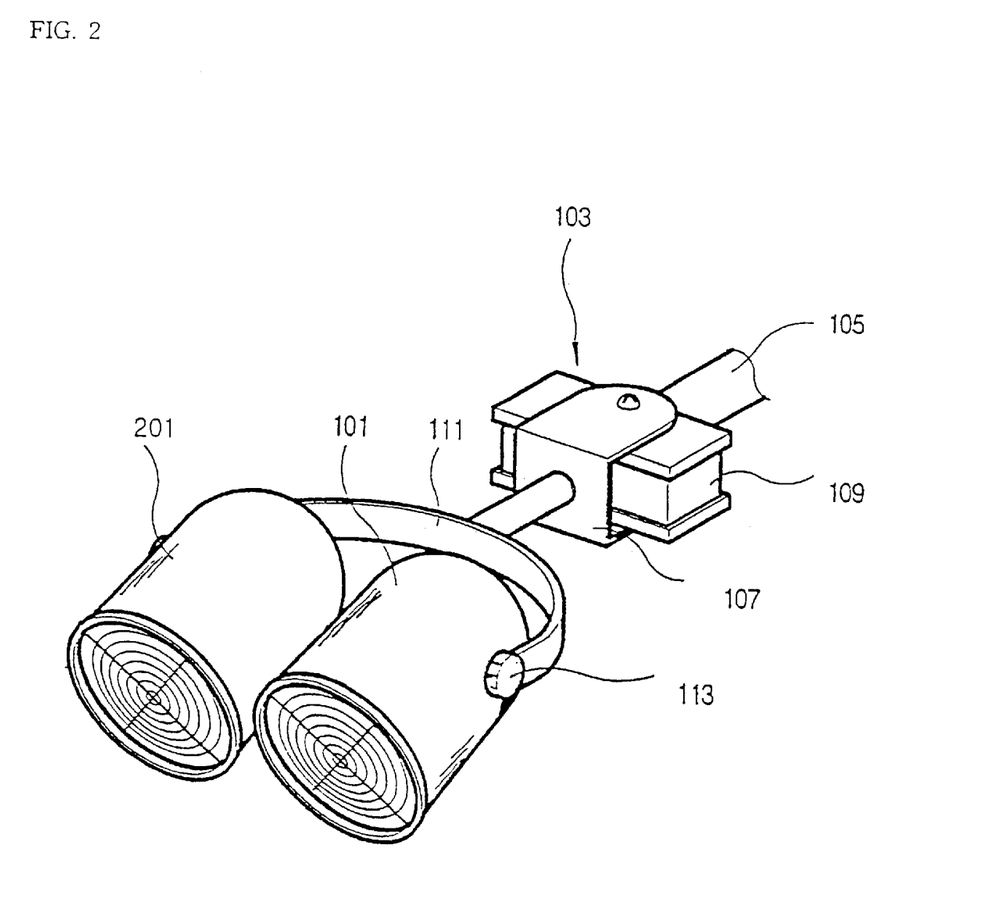
FIG. 2 is a perspective view showing a high-temperature radiating section and a low-temperature radiating section.

FIG. 1 is a block diagram illustrating a comprehensive constitution of a thermal treatment apparatus radiating low and high temperature according to a best mode 1 of the present invention. FIG. 2 is a perspective view showing a high-temperature radiating section and a low-temperature radiating section.

The thermal treatment apparatus radiating low and high temperature according to the present invention, comprises a high-temperature radiating section 101 for radiating high temperature, a low-temperature radiating section 201 for radiating low temperature, a rotating section 103 for rotating the high-temperature radiating section 101 and the low-temperature radiating section 201, and a supporting section 105 for supporting the high-temperature radiating section 101, the low-temperature radiating section 102 and the rotating section 103.

The control section 300 comprises a high-temperature radiating time control section (not shown in the drawings) for controlling the period of time for radiating high temperature by the high-temperature radiating section 101, a low-temperature radiating time control section (not shown in the drawings) for controlling the period of time for radiating low temperature by the low-temperature radiating section 201, and a rotation control section (not shown in the drawings) for controlling the period of time of rotation of the rotating section.

The high-temperature radiating section 101 comprises an infrared ray lamp or a far-infrared ray lamp commonly used in a thermal treatment apparatus.

Meanwhile, the low-temperature radiating section 201 comprises a cryo-pump, which is currently popular as a cryogenic temperature radiating device. The cryo-pump 207 is a device that can easily generate the temperature of minus tens of degrees centigrade without relying on the conventional liquefied coolant, and is widely used for the purpose of biological experiment, food preservation or manufacture of semiconductor devices. The low temperature is radiated if the cool air is flown into the low-temperature radiating section 201 through a hose 209, according to the present invention.

The high-temperature radiating time control section inside of the control section 300 has a construction that a power supply line 115 of the infrared ray lamp or far-infrared ray lamp in the high-temperature radiating section 101 is repeatedly turned on and off for a predetermined period of time. However, the construction may be embodied in diverse manners. For instance, controlling an interval of the pulses outputted from the timer IC and operating the mechanical relay with the pulse may be one of controlling the period of time for on/off of the lamp. The low-temperature radiating time control section is constructed so as to repeat the on/off of the cryo-pump during a predetermined period of time. FIG. 1 shows that a control line 213 is connected to the control section 300 for turning on/off of the cryo-pump in the low-temperature radiating section 200.

In the present invention, the high-temperature radiating power and the low-temperature radiating power are turned on/off in turns. For instance, if the high-temperature radiating time is set to be five seconds and the low-temperature radiating time is set to be three seconds the high-temperature radiating section operates for five seconds and is turned off. Then, the low-temperature radiating section operates for three seconds and is turned off. Subsequently, the high-temperature radiating section once again operates for five seconds. With these simple settings, high temperature and low temperature can be repeatedly irradiated onto the affected parts.

Such a layout can be implemented in diverse known manners. For example, a hardware can be constructed so that the on-cycle of the high-temperature radiating section be an off-cycle of the low-temperature radiating section and that the on-cycle of the low-temperature radiating section be an off-cycle of the high-temperature radiating section. Otherwise, a microcomputer can embody the same layout with a particular software program. Accordingly, one skilled in the art to which this invention pertains can easily conceive the same layout for operation.

The rotation control section of the control section 300 plays a function of controlling the period of rotating time of the high-temperature radiating section and the low-temperature radiating section through a user's manipulation. For instance, the rotation control section can control the speed of rotation by varying the resistance of a motor coil as in the manner of controlling a fan or by digitally varying the interval of the operating pulse, thereby varying the rms value of the operational electric power. This is the well-known technology that may be opted for by one skilled in the art. FIG. 1 shows that the control line 117 of the rotating section 103 is connected to the control section 300.

FIG. 2 shows that the high-temperature radiating section 101 and the low-temperature radiating section 201 are fixed onto the supporting section 105 by the rotating section 103. To be specific, the high-temperature radiating section 101 and the low-temperature radiating section 201 are fixed onto a yoke 107, which is coupled with a rotating axle of a motor 109. If the motor 109 is operated by fixing a body of the motor 109 onto the supporting section 105, the high-temperature radiating section 101 and the low-temperature radiating section 201 can rotate in horizontal direction centering around the supporting section 105.

While the above construction has been described with reference to a certain preferred embodiment, it will be understood by one skilled in the art that other constructions may be applicable to rotating the high/low-temperature radiating sections by centering around the supporting section.

FIG. 2 shows that the high-temperature radiating section 101 and the low-temperature radiating section 201 are movable in vertical direction. The joint 111 is fastened by a fixing knob 113 onto the high-temperature radiating section and the low-temperature radiating section. For instance, the radiating section is movable in vertical direction by protruding side surfaces of the respective radiating sections, forming penetrating holes on both ends of the joint 111, inserting the penetrating holes into a bolt, and fixing the bolt with the fixing knob 113 serving as a nut. This part is also a technical matter that can be easily conceived and applicable by one skilled in the art. Accordingly, the high-temperature radiating section 101 and the low-temperature radiating section 201 are horizontally rotatable by the motor and vertically movable through manipulation.

The thermal treatment apparatus according to the present invention having the above construction will now be described in further detail.

The height of the radiating section is adjusted in conformity with that of an affected part by adjusting the fixing knob 113 on side surfaces of the high-temperature radiating section 101 and the low-temperature radiating section 201. The high-temperature radiating section 101 and the low-temperature radiating section are placed nearby the affected part.

A panel of the control section 300 is manipulated for the purpose of setting the high-temperature radiating time and the low-temperature radiating time as well as the rotating time. As described above, if the high-temperature radiating time has been set to be five seconds and the low-temperature radiating time has been set to be three seconds, high temperature will be radiated for five seconds and low temperature will be radiated for three seconds. The same operations will be subsequently repeated.

Meanwhile, a shutter (not shown in the drawings) is installed at the low-temperature radiating opening of the low-temperature radiating section 201 so as to be closed when the cryo-pump is turned off. FIG. 1 shows that the control line 215 for controlling opening and closing of the shutter is connected between the low-temperature radiating section 201 and the control section 300, so as to completely block the cool air not instantly blocked but remained in the hose 209 even after turning off of the cryo-pump.

Installation of the shutter can also be easily carried out by one skilled in the art. For example, a blocking panel may be opened and closed in an electrical manner by installing a blocking panel operated by solenoid inside of the low-temperature radiating section, or in a mechanical manner by using a metal wire (like a brake wire in a bicycle) so as to be pulled or pushed.

(2) Best Mode 2

FIGS. 3a, 3b and 3c are external views showing constructions of the thermal treatment apparatus radiating low and high temperature according to a best mode 2 of the present invention, which is an improvement of the best mode 1.

In the best mode 1 shown in FIG. 1, the cryo-pump 207 and the control section 300 are separately installed, while the high-temperature radiating section 101 and the low-temperature radiating section 201 are rotated in horizontal direction by the motor 109 of the rotating section 103. In the best mode 2, by contrast, the cryo-pump and the control section are integrated into a single console 400, while the high-temperature radiating section and the low-temperature radiating section are movable forward, backward and in vertical direction as well. FIG. 3a is a top-plan view, FIG. 3b is a side-elevational view, and FIG. 3c is a front view.

The construction of the best mode 2 will now be explained with reference to FIG. 3. The thermal treatment apparatus according to the best mode 2 comprises a controlling console 400, a high-temperature radiating section 402 for radiating high temperature, a low-temperature radiating section 404 for radiating low temperature, and a lineal movement section for supporting and shifting the high-temperature radiating section 402 and the low-temperature radiating section 404 forward and backward.

The description of the high-temperature radiating section 402 and the low-temperature radiating section 404 will be omitted here because they are identical to those of the best mode 1.

The controlling console 400 performs the same function as the thermal treatment apparatus as shown in FIG. 1, except that the console includes a cryo-pump radiating cool air therein. Separation or combination of the cryo-pump and the control section is nothing more than a matter of modification that can be made within the technical scope of the present invention by one skilled in the art.

As in the case of the best mode 1, the controlling console 400 has a high-temperature radiating time control section for repeatedly turning on/off of the high-temperature radiating section 402 for a predetermined period of time, and a low-temperature radiating time control section for repeatedly turning on/off of cryo-pump for a predetermined period of time.

The lineal movement section supports and moves the high-temperature radiating section 402 and the low-temperature radiating section 404 forward and backward (X direction in FIG. 3b) with respect to the controlling console 400. The lineal movement of the high-temperature radiating section 402 and the low-temperature radiating section 404 can be simply realized in the rack and pinion manner.

Figure 4:
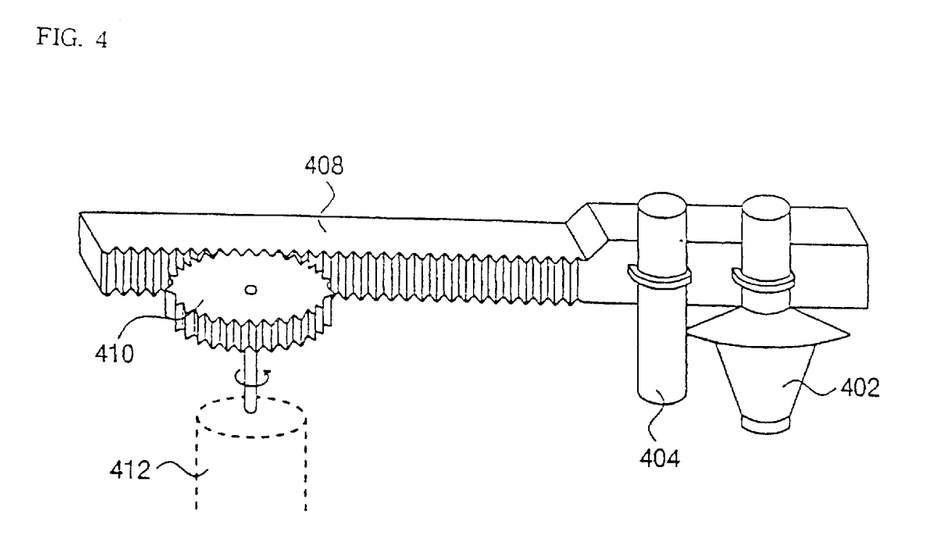
FIG. 4 is a conceptual view illustrating a mechanism of a lineal movement section according to the best mode 2 of the present invention.

As shown in FIG. 4, a rack 408 performs lineal reciprocating movements by means of a pinion 410 rotated by the motor 412. Thus, the high-temperature radiating section 402 and the low-temperature radiating section 404 can be moved forward and backward simply by controlling the motor 412 once after fixing the high-temperature radiating section 402 and the low-temperature radiating section 404 onto the rack 408. Here, the motor 412 can be controlled by the controlling console 400. It is preferable to use a stepped motor, which is easily controllable in its rotation in both directions, as a motor.

The lineal movement section 406 is fixed onto the controlling console 400 by means of the main axle 403. As will be explained later, the lineal movement section 406 can be moved in vertical direction by means of the main axle 403, and can be rotated in horizontal direction centering around the main axle 403. A cryo-pump discharging tube 418 is positioned at a rear side of the main axle 403. The cryo-pump discharging tube 418 is a tube discharging cool air of the cryo-pump installed inside of the controlling console 400, and comprises a flexible hose.

Figure 3:
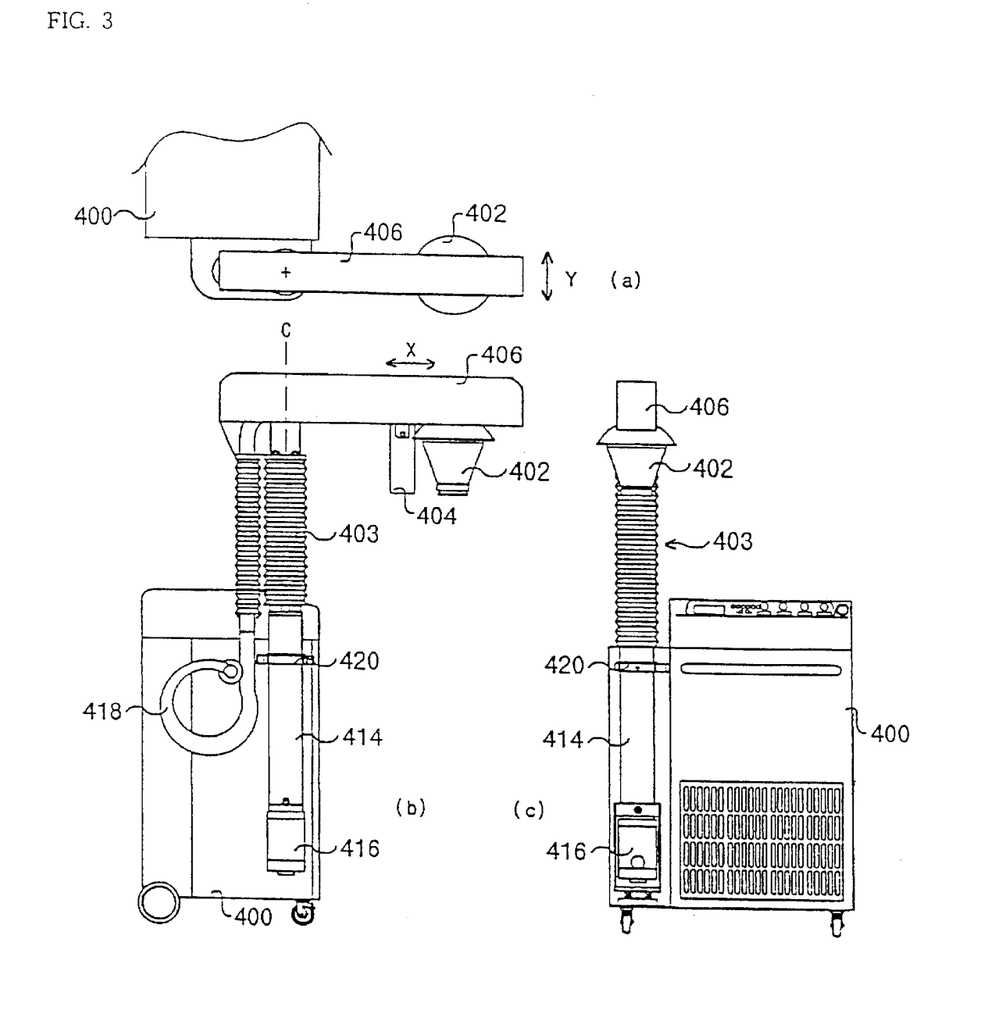
FIGS. 3a, 3b and 3c are external views showing constructions of a thermal treatment apparatus radiating low and high temperature according to a best mode 2 of the present invention.

While FIG. 3 shows a layout of the high-temperature radiating section 402 and the low-temperature radiating section 404 designed to lineally move forward and backward with respect to a front face of the controlling console 400, the present invention is not limited thereto. To be specific, the lineal movement section 406 is installed in horizontal direction (Y direction in FIG. 3a) with respect to the front surface of the controlling console 400 of the lineal movement section 406 so as to perform lineal reciprocating movements in horizontal direction with respect to the controlling console 400 of the high-temperature radiating section 402 and the low-temperature radiating section 404 by means of the rack and pinion.

Meanwhile, the best mode 2 additionally comprises a vertical movement section 414 for shifting the lineal movement section 406 in vertical direction, and a horizontal rotation section 416 for horizontally rotating the lineal movement section 406.

The vertical movement section 414 is an element for shifting the lineal movement section 406 itself in vertical direction with respect to the controlling console 400, as shown in FIGS. 3b and 3c, and can be realized by a power cylinder. To be specific, the vertical movement section 414 is vertically moved by fixing the power cylinder onto the controlling console 400 and by fixing the lineal movement section 406 onto a piston (not shown in the drawings) of the power cylinder. At this stage, the high-temperature radiating section 402 and the low-temperature radiating section 404 are movable in vertical direction. FIG. 2b shows that the lower end of the lineal movement section 406 is circularly wound so that the discharging tube 418 of the cryo-pump can freely move in vertical direction when the lineal movement section moves in vertical direction.

The horizontal rotation section 416 is an element for horizontally rotating the lineal movement section 406 by centering around the main axle 403 as a rotating axis C. FIG. 3 shows realization of a horizontal rotation section 416 by installing the motor at a lower end of the controlling console 400. In other words, the horizontal rotating section 414 rotates the power cylinder itself so that the lineal movement section 406 can horizontally rotate by centering around the rotating axis C. The discharging tube 418 of the cryo-pump, which has flexibility, flexibly changes its shape according to a rotation of the lineal movement section 406 in horizontal direction. Therefore, the lower end of the discharging tube 418 of the cryo-pump needs to be wound with sufficient space.

The horizontal rotation section 416 needs not comprise a motor. The motor may serve to electrically rotate the horizontal rotation section 416 through manipulation of the control section. However, manual rotation is also available in consideration of diverse advantages including the unit cost, structure and assembly. Use of a ball bearing serves for manual rotation of the lineal movement section 406. FIG. 3 shows that a clamp 420 is mounted on the controlling console 400 to prevent fluctuation occurring when the power cylinder 414 rotates.

The operation of the best mode 2 constructed above is the same as that of the best mode 1. In light of the best mode 1, it is also obvious that the shutter can also be closed when the cryo-pump is turned off, if the shutter is installed at the discharging hole of the low-temperature radiating section 404.

(3) Best Mode 3

Figure 5:
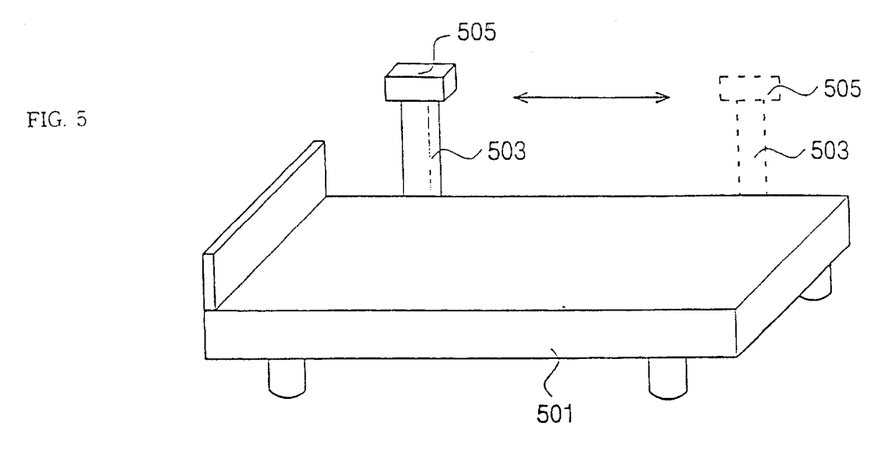
FIG. 5 is a schematic view of a thermal treatment apparatus radiating low and high temperature according to a best mode 3 of the present invention.

FIG. 5 shows an operational mechanism of a best mode 3 of the present invention. Whereas the best mode 2 shown in FIG. 3 has a construction that the lineal movement section 406, in which the high-temperature radiating section is combined with the low-temperature radiating section, rotates centering around C by being connected to the main axle 403, the best mode 3 has a construction that a main axle 503 connecting a head 505 and a controlling console 501 performs lineal reciprocating movements in horizontal direction. In the best mode 3, the controlling console 501 is manufactured to be used as a bed. Accordingly, if a user lies down the controlling console 501 of a bed shape, the main axle 503 performs a lineal movement from the side of the user, thereby irradiating low and high temperature onto the affected parts of the user.

As in the cases of the best mode 1 and the best mode 2, an elevator in the main axle 503 and a device for rotation and horizontal movement in a head 505 may also be applicable to the best mode 3. Meanwhile, the lineal movement in horizontal direction of the main axle 503 in the best mode 3 can be achieved by utilizing diverse kinds of known art. For example, the main axle 503 can be lineally and reciprocally moved subsequent to movement of the rack according to a rotation of the pinion by using the rack/pinion mechanism or by using a belt.

Figure 6A:
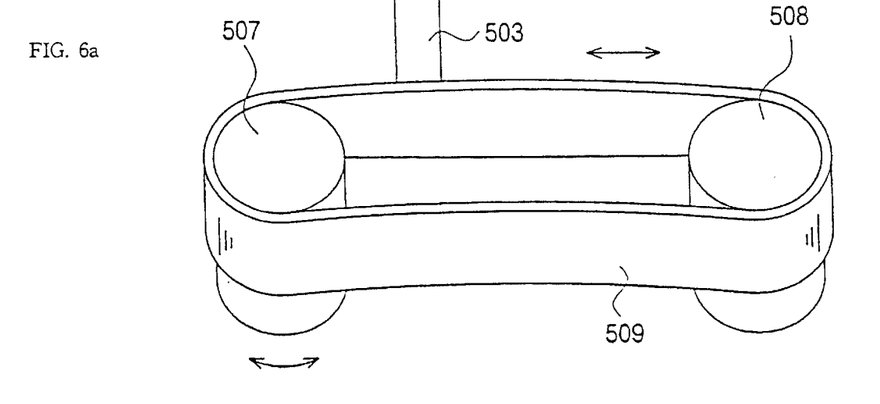
FIGS. 6a and 6b are conceptual views illustrating a mechanism of realizing the best mode 3 of the present invention.
Figure 6B:
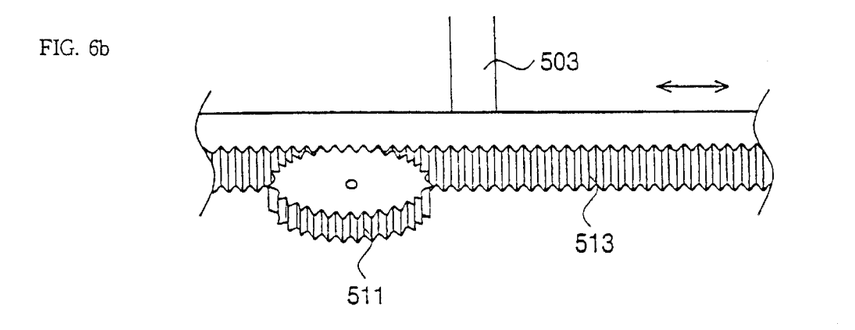

FIGS. 6a and 6b are conceptual views exemplifying a mechanism of horizontal movement of the main axle according to the best mode 3 of the present invention. FIG. 6a exemplifies use of a belt, and FIG. 6b exemplifies use of a rack and pinion. Referring to FIG. 6a, a belt 509 is wound between the operating roller 507 and the idle roller 508, while the main axle 503 is installed at the belt 509. The thermal treatment apparatus radiating low and high temperature is completed as shown in FIG. 5 by installing the belt inside of the controlling console 501 and by exposing the main axle 503 only. FIG. 6b shows a mechanism of performing the lineal movement centering around the main axle 503 by means of the rack and pinion. The rack 513, in which the main axle 503 is installed, can perform lineal reciprocating movements according to a rotation of the pinion gear 511.

As described above, the present invention enables repeated radiation of low and high temperature in turns. The present invention also enables irradiation of the low and high temperature onto affected parts through forward and backward movements as well as through movements in vertical and horizontal directions, thereby serving for an effective treatment of the affected parts.

The use of the present invention is not only applicable to treatment of a human but also to other purposes including sterilization of cosmetics or pharmaceuticals and tests of critical temperatures for survival of cells, etc. Moreover, the clinical tests for an object can also be performed by the apparatus according to the present invention, thereby serving for selecting materials (pharmaceuticals or other materials than pharmaceuticals) that can be administered into cells of the object by measuring the optimal adaptable temperature of the cells of the object.

What is claimed is:

1. A thermal treatment apparatus radiating low and high temperature, comprising:

a high-temperature radiating section for radiating high temperature;

a low-temperature radiating section installed around a periphery of the high-temperature radiating section for radiating low temperature;

a shifting section for shifting the high-temperature radiating section and the low-temperature radiating section; and a control section including a high-temperature radiating time control section for controlling on-time of the high-temperature radiating section, a low-temperature radiating time control section for controlling on-time of the low-temperature radiating section, and a shift control section for controlling shifting time of the shifting section, the control section controlling time for radiating high temperature by the high-temperature radiating section, time for radiating low temperature by the low-temperature radiating section, and shifting time by the shifting section.

2. The thermal treatment apparatus of claim 1, wherein the high-temperature radiating section is an infrared ray lamp or a far-infrared ray lamp, and the low-temperature radiating section radiates low temperature by being connected to a cryo-pump.

3. The thermal treatment apparatus of claim 1, wherein the shifting section includes a rotating section which comprises a joint for supporting the high-temperature radiating section and the low-temperature radiating section; a yoke coupled with the joint; and a motor coupled with a rotating axle for rotating the yoke, the rotating section being characterized in that the high-temperature radiating section and the low-temperature radiating section coupled with the yoke and the joint rotate in horizontal direction according to a rotation of the motor.

4. The thermal treatment apparatus of claim 3, wherein the joint, the high-temperature radiating section and the low-temperature radiating section are fixed onto a fixing knob so that the high-temperature radiating section and the low-temperature radiating section can be moved in vertical direction.

5. The thermal treatment apparatus of claim 1, wherein the shifting section includes a lineal movement section which comprises a motor, a pinion coupled with an axle of the motor so as to rotate, and a rack lineally moved according to a rotation of the pinion by being engaged therewith, the lineal movement section being characterized in that the high-temperature radiating section and the low-temperature radiating section fixed onto the rack perform lineal movements according to a rotation of the motor.

6. The thermal treatment apparatus of claim 5, wherein the rack lineally moves in forward and backward directions (X direction).

7. The thermal treatment apparatus of claim 5, wherein the rack lineally moves in horizontal direction (Y direction).

8. The thermal treatment apparatus as in claim 5, wherein the shifting section further comprises:
   a vertical movement section including a main axle for supporting the lineal movement section, and a power cylinder for lineally shifting the lineal movement section in vertical direction by centering around the main axle as a piston; and
   a horizontal movement section for rotating the power cylinder in horizontal direction.

9. The thermal treatment apparatus of claim 1, wherein the shifting section comprises a main axle, on which the high-temperature radiating section and the low-temperature radiating section are mounted, and means for performing lineal reciprocating movements in horizontal direction centering around the main axle.

10. The thermal treatment apparatus of claim 9, wherein the means for performing lineal reciprocating movements in horizontal direction, comprises a driving roller, an idle roller, a belt connected between the driving roller and the idle roller, and a main axle fixed onto the belt.

11. The thermal treatment apparatus of claim 9, wherein the means for performing lineal reciprocating movements in horizontal direction, comprises a pinion, and a rack coupled with the pinion and the main axle.

12. The thermal treatment apparatus of claim 1, wherein the low-temperature radiating section comprises a shutter for being closed when a low-temperature radiating time is over so as to completely block radiation of the low temperature remained in the low-temperature radiating section.

13. The thermal treatment apparatus of claim 3, wherein the low-temperature radiating section comprises a shutter for being closed when a low-temperature radiating time is over so as to completely block radiation of the low temperature remained in the low-temperature radiating section.

14. The thermal treatment apparatus of claim 5, wherein the low-temperature radiating section comprises a shutter for being closed when a low-temperature radiating time is over so as to completely block radiation of the low temperature remained in the low-temperature radiating section.

15. The thermal treatment apparatus of claim 9, wherein the low-temperature radiating section comprises a shutter for being closed when a low-temperature radiating time is over so as to completely block radiation of the low temperature remained in the low-temperature radiating section.

16. The thermal treatment apparatus of claim 2, wherein the shifting section includes a rotating section which comprises a joint for supporting the high-temperature radiating section and the low-temperature radiating section; a yoke coupled with the joint; and a motor coupled with a rotating axle for rotating the yoke,
   the rotating section being characterized in that the high-temperature radiating section and the low-temperature radiating section coupled with the yoke and the joint rotate in horizontal direction according to a rotation of the motor.

17. The thermal treatment apparatus of claim 2, wherein the shifting section includes a lineal movement section which comprises a motor, a pinion coupled with an axle of the motor so as to rotate, and a rack lineally moved according to a rotation of the pinion by being engaged therewith,
   the lineal movement section being characterized in that the high-temperature radiating section and the low-temperature radiating section fixed onto the rack perform lineal movements according to a rotation of the motor.

18. The thermal treatment apparatus of claim 2, wherein the shifting section comprises a main axle, on which the high-temperature radiating section and the low-temperature radiating section are mounted, and means for performing lineal reciprocating movements in horizontal direction centering around the main axle.

19. The thermal treatment apparatus of claim 2, wherein the low-temperature radiating section comprises a shutter for being closed when a low-temperature radiating time is over so as to completely block radiation of the low temperature remained in the low-temperature radiating section.

20. The thermal treatment apparatus as in claim 6, wherein the shifting section further comprises:
   a vertical movement section including a main axle for supporting the lineal movement section, and a power cylinder for lineally shifting the lineal movement section in vertical direction by centering around the main axle as a piston; and
   a horizontal movement section for rotating the power cylinder in horizontal direction.

* * * * *